US006190313B1

(12) United States Patent
Hinkle

(10) Patent No.: US 6,190,313 B1
(45) Date of Patent: Feb. 20, 2001

(54) INTERACTIVE HEALTH CARE SYSTEM AND METHOD

(76) Inventor: Allen J. Hinkle, 65 Jenkins Rd., Lebanon, NH (US) 03766

( * ) Notice: Under 35 U.S.C. 154(b), the term of this patent shall be extended for 0 days.

(21) Appl. No.: 09/062,810

(22) Filed: Apr. 20, 1998

(51) Int. Cl.[7] .................................................. A61B 5/00
(52) U.S. Cl. .............................. 600/300; 705/2; 128/903; 600/301; 600/529
(58) Field of Search .................................. 600/300, 301; 128/903, 904, 920–923; 705/1–3; 706/1–44

(56) References Cited

U.S. PATENT DOCUMENTS

| | | | |
|---|---|---|---|
| 5,257,206 | 10/1993 | Hanson | 364/502 |
| 5,410,471 | 4/1995 | Alyfuku et al. | 364/413.02 |
| 5,440,478 | 8/1995 | Fisher et al. | 364/188 |
| 5,486,999 | 1/1996 | Mebane | 364/401 |
| 5,524,645 | 6/1996 | Wills | 128/898 |
| 5,612,869 | 3/1997 | Letzt et al. | 395/203 |
| 5,619,991 * | 4/1997 | Sloane | 600/300 |
| 5,626,144 | 5/1997 | Tacklind | 128/725 |
| 5,671,734 * | 9/1997 | Pugh | 600/301 |

OTHER PUBLICATIONS

"Welcome to The AirWatch Airway Monitoring System—User Guide", ENACT Health Management Systems, Inc., Palo Alto, 1995.

"Economic Control of Quality of Manufactured Product", W.A. Shewhart, D. Van Nostrand Co., Inc. 1931; repr. ed. American Society for Quality Control, Milwaukee, 1980; pp. iii–xiv.

* cited by examiner

Primary Examiner—Cary O'Connor
Assistant Examiner—Michael Astorino
(74) Attorney, Agent, or Firm—Michael J. Weins; Jeffrey E. Semprebor

(57) ABSTRACT

A system and related method for remotely monitoring the health of a patient are provided to inform the patient as to his/her state of health. Data on a patient physiological parameter is analyzed at a patient site using Shewhart's rules of detection. The patient is notified when the conditions for one of Shewhart's rules are met, which may indicate a significant change in the patient's health status. Preferably, the notice to the patient is tailored by the patient's health care provider, and may instruct the patient to contact the health care provider or take some other preventative action. Preferably, information is transferred from the patient site to a health care provider site. An elementary system has a patient operated sensor for taking physiological measurements and converting them into an indexed data record, a patient site data processing unit with a database for storing such indexed data records, and a SPC instruction set which enables the patient site data processing unit to perform a SPC analysis on the indexed data records to determine if Shewhart's rules are met. Means for notifying the patient that one of Shewhart's rules is met are also provided.

10 Claims, 7 Drawing Sheets

INTERACTIVE HEALTH CARE SYSTEM AND METHOD

FIELD OF THE INVENTION

The present invention relates to a system and method for monitoring the health status of a patient at the site of the patient and providing the patient with an evaluation of such health status to allow the patient to take an interactive role in his/her own health care.

BACKGROUND OF THE INVENTION

With the advances in instrumentation it is possible to monitor patients from remote locations, allowing more frequent measurements of one or more physiological parameters related to the patient's health condition. This remote monitoring brings two benefits to the patients. First, remote monitoring is less disruptive to the patient's life style and, second, remote monitoring can provide more representative values of the patient's state of health, since the values are being measured in a familiar environment.

Monitoring patients is frequently done for patients being treated for a chronic health condition. For patients being treated for a chronic health condition, monitoring allows the patient's health care provider to monitor the health status of the patient and adjust the treatment of the patient accordingly. Similarly, monitoring is helpful in treating an acute health condition which may be temporary or intermittent. Monitoring can also be helpful to individuals who are on a health care maintenance program rather than a treatment program. In this case, monitoring is useful in evaluating the effectiveness of the health care maintenance program.

U.S. Pat. No. 5,410,471 is directed to a passive patient monitoring system which provides various sensors which operate in non-medical environments. These sensors also record personal identification information and encode it with the measurement data so that the source of the data can be identified. The sensors can be provided with memory and linked together with other sensors and instruments to provide a network which can utilize the data to track the state of health of the patient. The encoded data is transmitted to a central location for processing and evaluation, and can optionally be displayed on a monitor at the patient's site. While the '471 patent does teach sharing the information collected, it does not provide a method for evaluating the data or making such evaluation available to the patient.

U.S. Pat. No. 5,626,144 teaches another system which employs remote sensors to monitor the state of health of a patient. This system differs in part from the system of the '471 patent in that the patient is not only aware of the testing, but actively participates in the testing. The system taught in the '144 patent is commercially provided by ENACT Health Management Systems, Inc., under the trademark AirWatch™. The '144 patent discloses a remote patient-operated air flow meter which has a memory for recording, tagging, and storing a limited number of test results. The patient-operated air flow meter also has a display to allow the patient to view a series of normalized values, and provides a warning when the value falls below a prescribed percentage of a "personal best number" value previously set by the patient. The patient-operated air flow meter also includes a modem for transmission of the tagged data over the telephone to a remote computer for downloading and storing in a relational database. The '144 patent also teaches that the remote computer can be employed to analyze the data. This analysis can then be provided as a report to the health care provider and/or to the patient.

While the '144 patent does offer some rudimentary indication of the patient's state of health, and in particular for asthma, it does so based on an individual reading which is compared to a preset "personal best number". The "personal best number" is defined in the user guide for the AirWatch™ device as "the Peak Flow reading that you can usually measure with your AirWatch monitor when your airway is clear and your breathing is good." Thus, this preset "personal best number" is a subjective value which may or may not provide an adequate index of the patient's health status. If the patient wishes a more objective indication of his/her state of health, such can only be obtained based on an analysis done at a remote location, and this information is historically based, providing little information which could help the patient take actions prior to the occurrence of a health crisis to avoid the same.

Thus, there is a need for a patient orientated system which allows the patient to take greater responsibility for his/her state of health. Such a system should provide a method of analyzing the patient's health measurement data which provides advance warning of a potential health crisis. The system should also use the analysis to provide guidance to the patient as to a course of action to be pursued to prevent the potential health crisis. Preferably, such a patient oriented system provides for automatic updating of the health care provider as to the status of the patient and as to whether intervention is required on the part of the health care provider.

SUMMARY OF THE INVENTION

The present invention provides a method of evaluation of the state of health of a patient under the supervision of a health care provider, where the patient measures a physiological parameter which is indicative of his/her health. The invention also provides a system for monitoring the state of health of the patient which utilizes the method and does not require interaction with the health care provider to inform the patient as to his/her state of health.

The method collects and records data on one or more physiological parameters of a patient and analyze the data on an ongoing basis as the data becomes available. This data is preferably supplied to the patient's health care provider so that it is available for review and analysis by the health care provider.

In the case that a larger health care community interest such as a health maintenance organization (HMO) is involved, such should also be provided the data for its analysis. This gives the HMO the ability to conduct various analyses of the data to determine the statistical effectiveness of a certain treatment program which is used for a number of patients, comparing the relative effectiveness of different health care providers, discovering seasonal or locational factors which effect health status, etc. The results of such analyses by the HMO can then be provided to the health care providers and individual patients to assist them in developing more effective treatment programs for maintaining the health of the patients.

To evaluate the state of health of the patient, the data is analyzed using the principles of statistical process control (SPC) analysis. The principles of SPC in detecting special cause variations in industrial processes to indicate when the industrial process is not stable within its control limits is further discussed in *Economic Control of Quality of Manufactured Product* by Walter A. Shewhart (Van Nostrand, 1931; repr. ed., American Society for Quality Control, 1980.) Over the years, these principles have been distilled into Shewhart's rules of detection. The present invention applies the principles of Shewhart's rules, which have classically been used for industrial quality control, for monitoring health status. Preferably, control charts are used to assist the patient and the health care provider in identifying when the conditions for one of Shewhart's rules of detection is met.

When one of Shewhart's rules is met, notice is provided to the patient that a special cause variation has occurred. Depending on the health condition being monitored and the control limit which the data are approaching or exceeding, such special cause variation may indicate a significant change in the health status of the patient. These changes may result in improvement or deterioration of the health of the patient. When improvement is indicated, the patient is notified that the health maintenance program of the patient may need to be changed in view of such improvement, and/or that a previous corrective action has been effective. When deterioration is indicated, the patient is notified that corrective action should be taken to prevent a health crisis. Preferably, the notice of action to the patient is tailored by the patient's health care provider based on the rule which is met as well as to the direction of the special cause variation.

Since a special cause variation is indicative of the data point values approaching or exceeding one of the control limits, the direction is defined by the control limit which the data point values appear to be approaching or exceeding. In many cases, a special cause variation in the direction of one of the limits is desirable, indicating improvement of the patient's health condition, while a special cause variation in the direction of the other control limit is undesirable, indicating deterioration of the patient's health condition.

In an elementary form of the method, the notice in all cases is that the health care provider should be contacted. When contacted, the health care provider provides guidance to the patient by directly advising the patient as to what further action to take.

Alternatively, in a preferred method which provides the patient greater responsibility in his/her care, a table of alternate instructions is prepared by the health care provider. The instructions are keyed to the direction of the special cause variation, as well as being keyed to the rules of detection. In such cases, the message associated with the rule violated is provided to the patient to advise as to a course of action to be taken. When the table of alternate instructions is employed, the method is well suited for implementation through a computer-based system.

A system which is capable of practicing the method, in an elementary form, has at least one patient operated sensor for taking physiological measurements from a patient and converting it into an indexed data record, a patient site data processing unit which has an associated database for storing indexed data records from the at least one patient operated sensor, and a SPC instruction set for the patient site data processing unit. The SPC instruction set enables the patient site data processing unit to selectively perform a SPC analysis on the indexed data records to determine if one or more of Shewhart's rules of detection are met. Means for notifying the patient that one or more of Shewhart's rules of detection are met are also provided.

The patient operated sensor, which takes measurements of a physiological parameter of the patient, has means for converting each measurement into an indexed record which is preferably time-stamped. In situations where multiple patients are using the one or more patient operated sensors, the indexed data record has tags which identify the individuals. Similarly, if more than one type of sensor is being used to collect more than one type of data, the tag includes the nature of the measurement being taken (blood pressure, air flow, air volume, etc.).

The patient site data processing unit may be either a dedicated microprocessor or a microcomputer. Employing a microcomputer allows for additional features, as is discussed below. In either case, the patient site data processing unit employs a database which is compatible with the data processing unit and the size and complexity of the data. For a patient site data processing unit which is dedicated to a single patient, a spread sheet format readily handles the data. As the number of variables being monitored is increased, or when the patient site data processing unit is shared by multiple patients, it is preferred for a relational database to be employed to store the data, in order to facilitate searching and processing.

The form of the SPC instruction set for the patient site data processing unit also depends on the patient site data processing unit employed, and can range from a ROM to a software program which is read by the patient site data processing unit. The SPC instruction set in all cases enables the patient site data processing unit to selectively perform a SPC analysis on the indexed data records and determine whether the conditions of any of Shewhart's rules of detection are met.

The means for notifying the patient when one or more of Shewhart's rules of detection are met can take on various forms. These forms are frequently software based and provide an external signal such as a sound, printed message, or a message on a monitor.

In a preferred embodiment, means for transferring information (either the analyzed data or, more preferably, the indexed data records) from the patient site data processing unit to a health care provider site are provided. At the health care provider site, the data can be evaluated to provide for professional review and/or analysis.

When the patient site data processing unit is a microcomputer and the health care provider site has a microcomputer, it is preferred to have a means for communication therebetween. It is still further preferred to provide a bi-directional message center which allows the patient, through his/her computer, and the health care provider, through its computer, to exchange what each party considers relevant to communicate with each other regarding the state of health of the patient.

A preferred means for notifying the patient when one or more of the Shewhart's rules are met includes a patient look-up table with messages tailored by the health care provider to the individual patient identified, the direction in which the special cause variation occurred, the rule violated, and the type of data analyzed. Preferably, a master look-up table is resident in the health care provider's microcomputer, and the message fields are addressable through the microcomputer to allow the health care provider to adjust the message provided to the patient as the health care provider sees changes in conditions developing through his/her evaluation of the data. The relevant portion of the master look-up table is downloadable by the patient microcomputer and downloads any changed information relevant to its site whenever the health care provider's microcomputer is accessed.

When the health care provider is provided with a microcomputer, it is preferred for the data for each patient to be stored in a health cared provider database. The size of the health care provider database and its complexity determines whether a relational database should be employed. The health care provider database offers the health care provider an opportunity to analyze the data of various patients to establish if there is a community health standard which results in violation of Shewhart's rules, or whether a problem is isolated to a particular individual.

It is also preferred that, when the health care provider is part of a larger health care community such as a health maintenance organization (HMO), the HMO maintains an HMO database which has data that is tagged to also include the identification of the health care providers for the patients from which the data was received. In the case that there is an HMO, the database is both complex and large, and thus it is generally preferred that the database of the HMO be a relational database.

When there is an HMO, it is preferred that a line of communication is maintained between the patients, the health care providers, and the HMO. These communication lines could be via modems directly linking the various computers together via telephone, Internet links, or direct connection through a LAN network. In the latter case, the patients, the health care providers, and the HMO could be connected by a LAN similar to that taught in the '471 patent.

The HMO preferably has a data processing capability, as well as instructions to allow the HMO data processor to operate on the HMO relational database to conduct various analyses of the data.

BRIEF DESCRIPTION OF THE FIGURES

FIG. 5 indicates X values which resulted in the conditions for one of Shewhart's rules being met, illustrating the predictive ability of the method.

BEST MODE OF CARRYING THE INVENTION INTO PRACTICE

Figure 1:
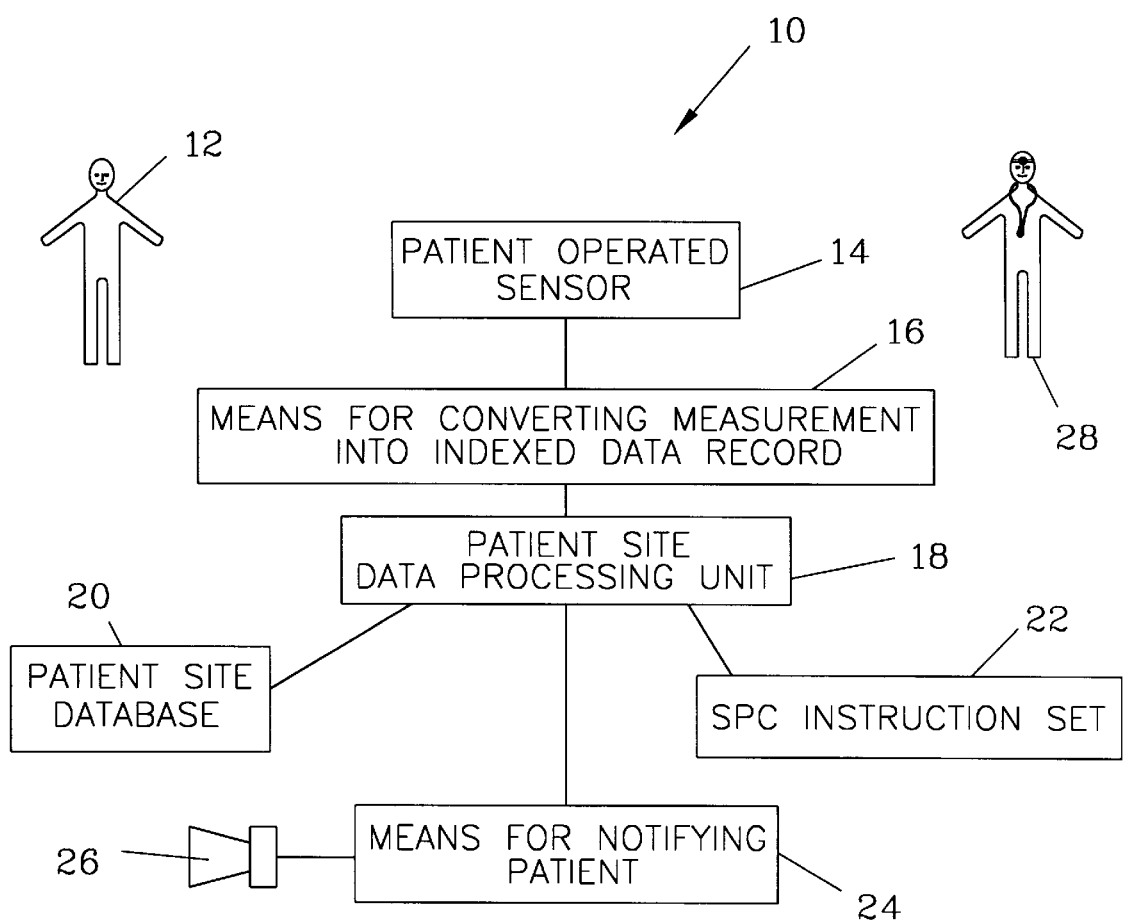
FIG. 1 illustrates a health care system having a patient operated sensor (a flow meter) for measuring a physiological measurement (peak expiratory flow), and means for converting the measurement into an indexed data record. A patient site data processing unit is provided, which has an associated database in which the indexed data records are stored. A SPC instruction set directs the patient based data processing unit to analyze the database to determine whether one or more of the Shewhart's rules of detection are met. A speaker is provided to provide notice to the patient that one of the Shewhart's rules of detection have been violated.

FIG. 1 is one embodiment of a health care system 10 where a patient 12 has an interactive role in the management of his/her state of health. The health care system 10 has a patient operated sensor 14, which for this embodiment is a peak flow meter such as is described in the '144 patent. The patient operated sensor 14 allows measurement of a physiological parameter of the patient 12, and in the embodiment shown the patient operated sensor 14 measures peak expiratory flow. Means for converting the measurement into an indexed data record 16 are provided. The means 16 can be made an integral part of the sensor system, as has been done with the ENACT AirWatch™ airway monitoring system, which is a commercial product based on the '144 patent.

A data processing unit 18 is provided. A programmable microprocessor serves as a data processing unit 18, which has an associated patient site database 20, in which the indexed data records are stored. Both the data processing unit 18 and the patient site database 20 can be provided in the patient operated sensor 14. A SPC instruction set 22 is provided, which directs the data processing unit 18 to analyze the indexed records in the patient site database 20 and to determine whether one or more of the Shewhart's rules of detection are met. The instruction set 22 can be maintained on a ROM included on a chip which also contains the data processing unit 18 and the patient site database 20.

Means for notifying the patient when the rules have been met 24 are provided. These means 24 can be software which generate signals for a speaker 26 to provide an audible signal. When such a notice is provided, the patient 12 should contact a health care provider 28. Preferably, the patient 12 also provides the data to the health care provider 28 for further analysis and review.

While the above described rudimentary health care system 10 allows the patient to monitor his/her state of health, any interaction with the health care provider 28 must be initiated by the patient 12. It is preferred to have an interactive health care system where there is joint monitoring and shared responsibility for the management of the patient's state of health between the patient 12 and the health care provider 28. Such a system provides greater safety for the patient 12, and is especially desirable for a patient 12 whose physical and/or mental functioning may be impaired.

Figure 2:
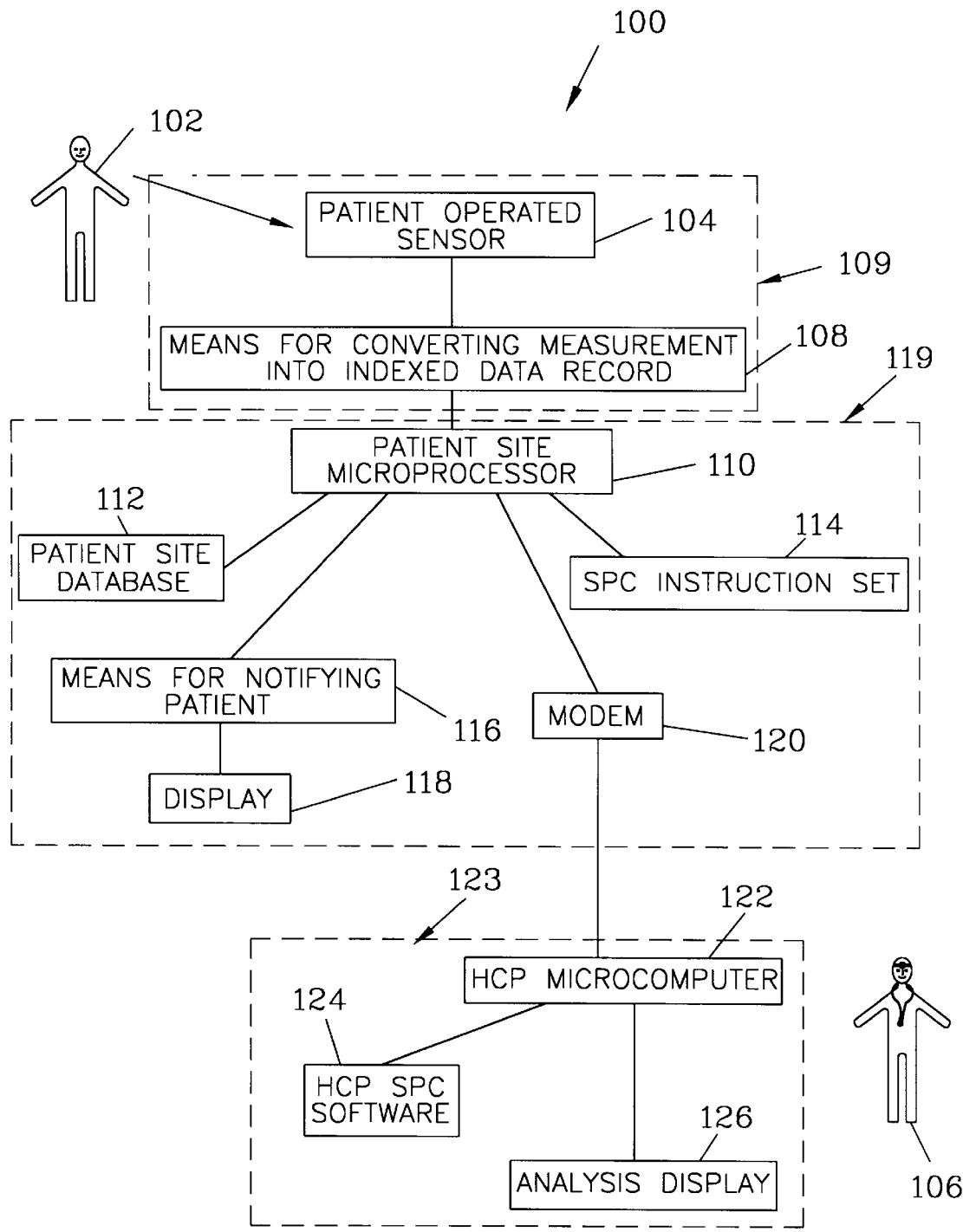
FIG. 2 illustrates a patient-health care provider interactive health care system which allows information to be shared between a patient and a health care provider (HCP). A microprocessor serves as a patient site data processing unit, having an associated database and an instruction set for enabling the microprocessor to perform a SPC analysis of the data. A display is provided for notifying the patient when one or more of Shewhart's rules of detection are met. A modem allows for periodically accessing the information in the patient database by a health care provider microcomputer, where the data can be independently processed by employing SPC software, and the results reported a health care provider display.

FIG. 2 illustrates a patient-HCP interactive health care system 100 which allows the information generated by a patient 102 using a patient operated sensor 104 to be shared between the patient 102 and a health care provider 106. In this embodiment, the patient operated sensor 104 for taking physiological measurements and a means for converting the measurement into an indexed record 108 are contained in a common sensor case 109. A microprocessor 110 serves as a data processing unit and has an associated patient site database 112. In single sensor devices, such as illustrated in FIG. 2, there are relatively few data points and the data can be readily handled by a simple database such as is used for spreadsheets.

A SPC instruction set 114 is provided for enabling the microprocessor 110 to operate on the patient site database 112, perform an SPC analysis of the indexed data records, and determine whether one or more of Shewhart's rules of detection are met. Again, the instruction set 114 can be maintained on a ROM included on a chip also containing the microprocessor 110 and the patient site database 112. Means for notifying the patient when the rules have been met 116 are provided, which generate a viewable signal shown on a display 118. When such notice is provided, the patient 102 should contact the health care provider 106.

The microprocessor 110, the patient site database 112, the SPC instruction set 114, the means for notifying the patient 116, and the display 118 preferably reside at a patient site 119. When a microprocessor is employed as a data processing unit and only a single patient operated sensor is employed, the patient site 119 and the common sensor case 109 may be contained in a single unit for greater convenience and portability.

Figure 5:
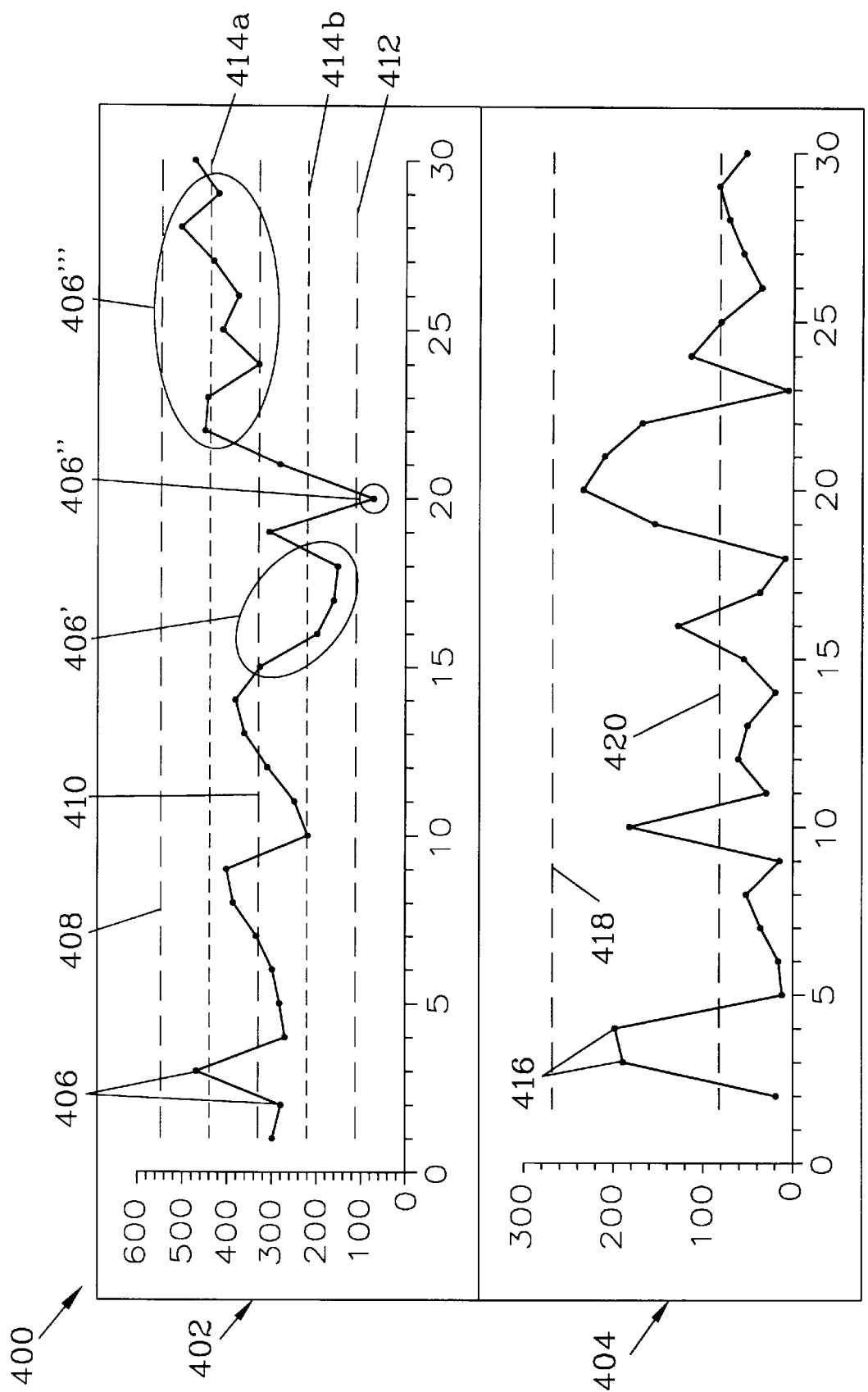
FIG. 5 shows an example of an XmR chart displaying peak expiratory flow (PEF) data for a patient with asthma which was processed retrospectively using the method of the present invention. The XmR chart has an upper part, which displays observed X values, an upper process control limit, a process center line, a lower process control limit, and two midway lines. The XmR chart also has a lower part which displays calculated mR values, an upper limit of the moving range, and an average moving range.
Figure 6:
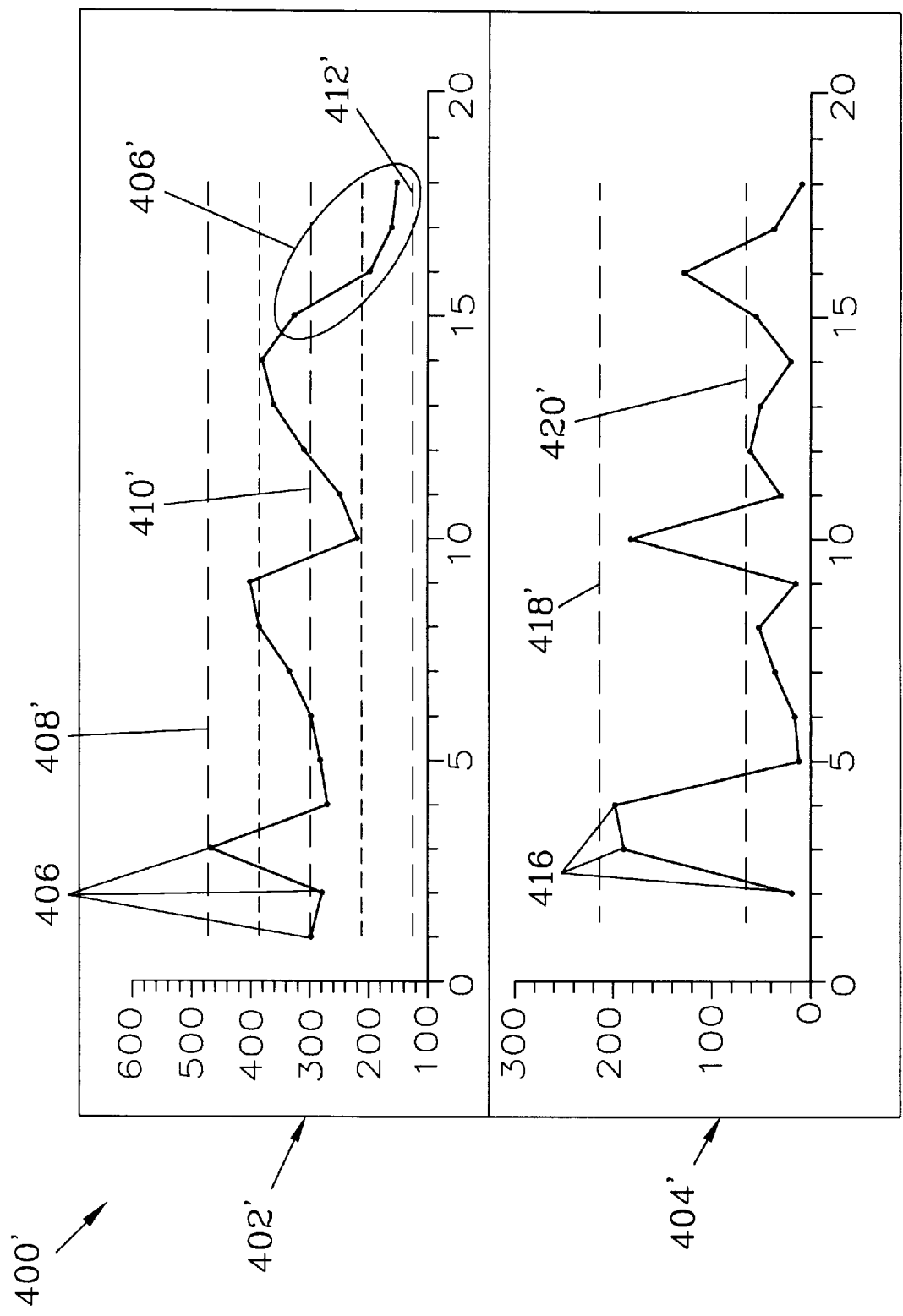
FIG. 6 shows an alternative XmR chart displaying the first eighteen data points shown in FIG. 5; this XmR chart shows control limits which are calculated from these eighteen data to illustrate the benefit of recalculating the control limits as each data point is entered. Using the method of the present invention would have provided advance notice to the patient prior to a critical health condition being reached.
Figure 7:
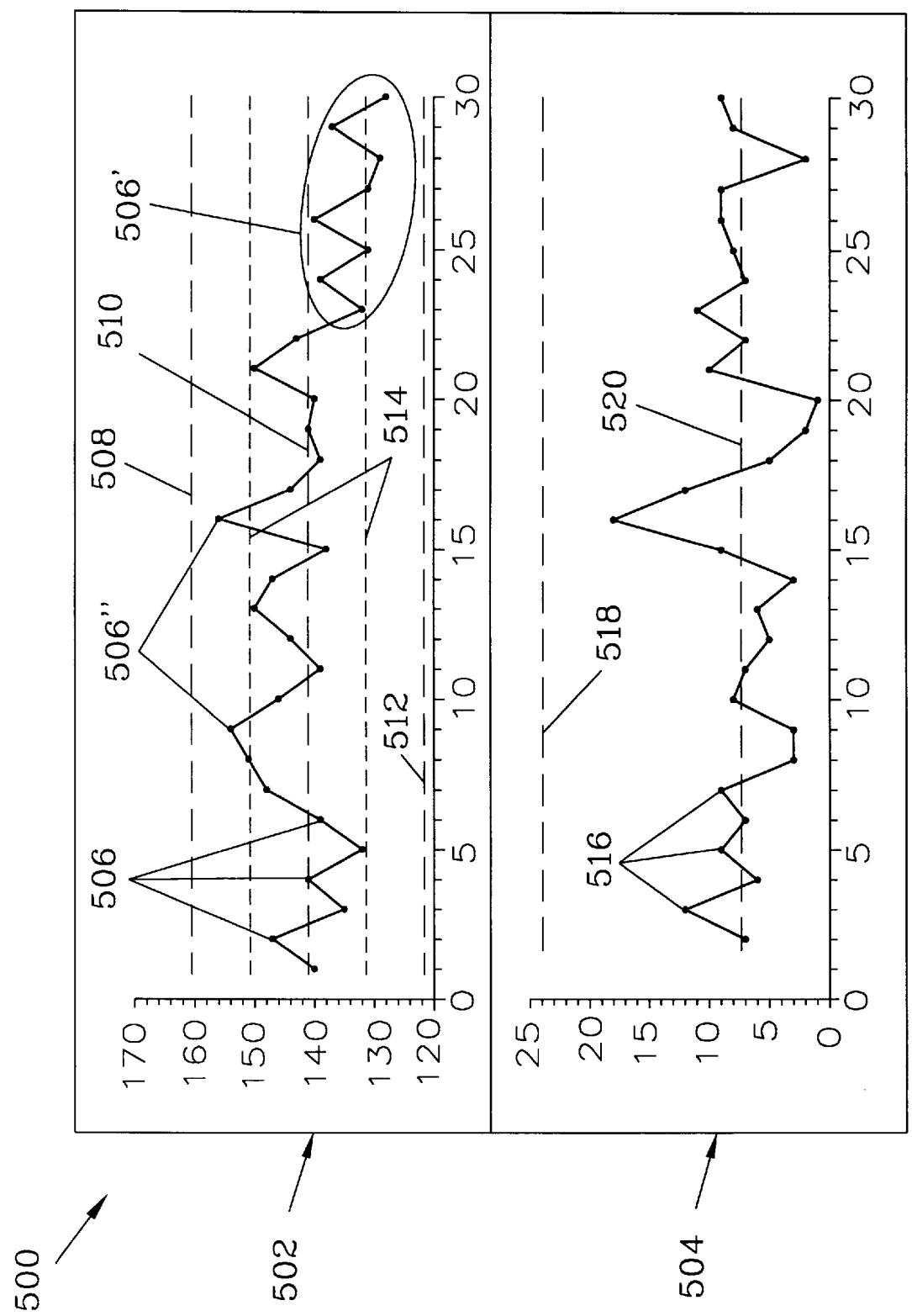
FIG. 7 shows another example of an XmR chart, this one displaying blood glucose level data for a patient with diabetes, which was analyzed and displayed in a similar manner to the data shown in FIG. 5.

The microprocessor 110 of the health care system 100 is connected to a modem 120, which preferably also resides at the patient site 119. The modem 120 includes a dial-up routine allowing the patient 102 to periodically communicate the indexed data records in the patient site database 112 to a health care provider microcomputer 122, located at a health care provider site 123. This data can the n be processed by the health care provider microcomputer 122 by employing health care provider SPC software 124, and the results reported on an analysis display 126. It is preferred that the results be correlated by charting the data and the moving range between data values as a function of time for viewing on the analysis display 126. FIGS. 5 through 7 illustrate typical control charts which might be displayed. By visual inspection of such charts, the health care provider 106 can identify when the rules of detection are met. With this information, the health care provider 106 can contact the patient 102 to provide instruction on what corrective action should be taken.

Figure 3:
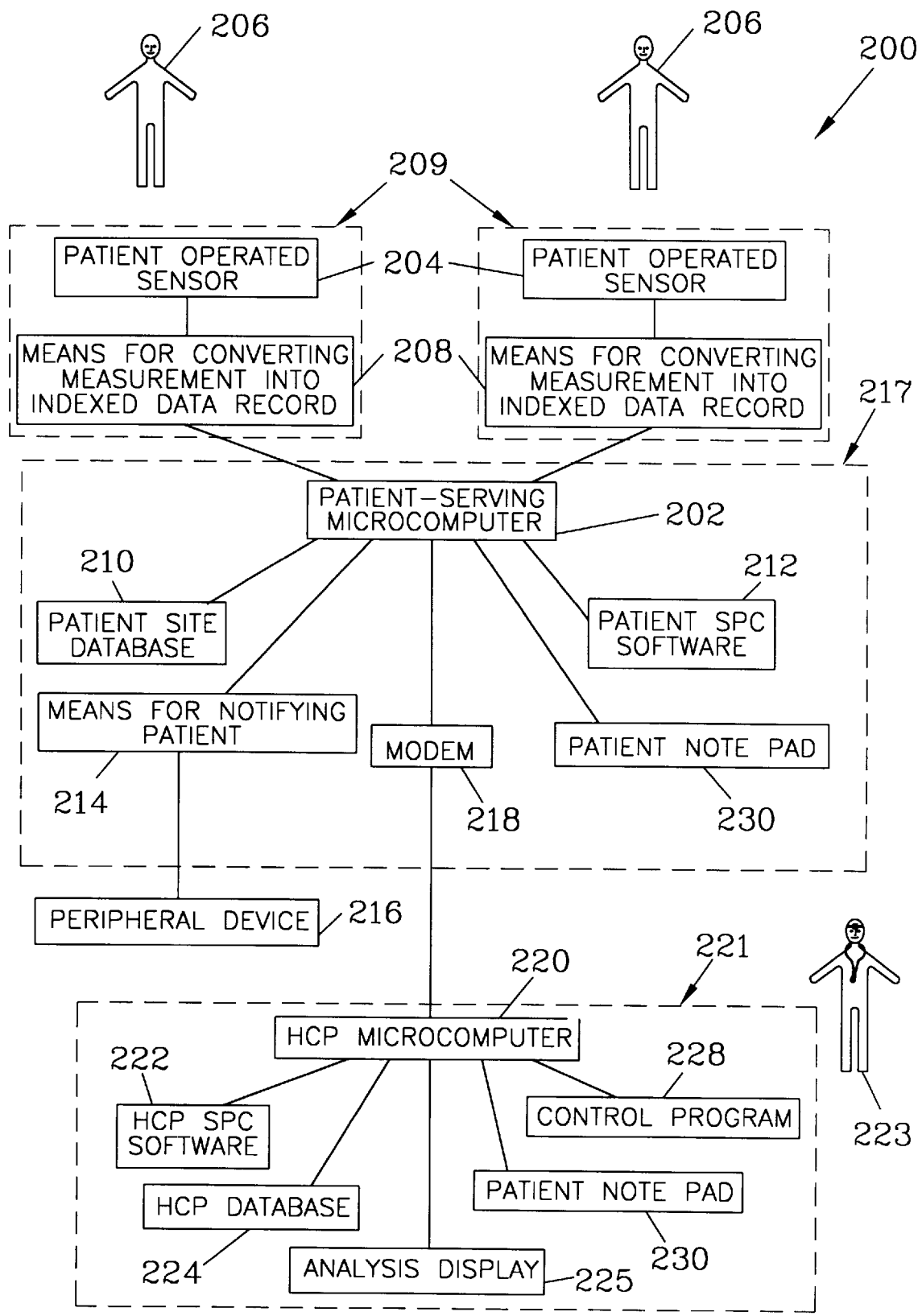
FIG. 3 is a patient-HCP interactive health care system in which a patient-serving microcomputer services multiple patient operated sensors, allowing a group of patients to be monitored. Each of the patient operated sensors has a means for converting a measurement into an indexed record which includes the type of sensor data recorded and a patient identifier code. SPC software instructs the patient-serving microcomputer to selectively perform the SPC analysis of the indexed records, and identify when the rules are met. The patient-serving microcomputer can provide notice when the rules are met through a peripheral device. A modem provides a communication link between the patient-serving microcomputer and a health care provider microcomputer, and allows the transfer of data from a patient database to a health care provider database for analysis with health care provider SPC software. The health care provider also has a control program which allows adjusting the SPC software in the patient-serving microcomputer as the status of the patients changes, and also allows adjusting the messages which are sent to the peripheral device.

FIG. 3 is an patient-HCP interactive health care system 200 which differs in part from the embodiment of FIG. 2 in that the microprocessor 110 used to process data has been replaced with a patient-serving microcomputer 202. The patient-HCP interactive health care system 200 also differs in that the patient-serving microcomputer 202 is not dedicated to a single sensor or to a single patient. In the patient-HCP interactive health care system 200, the patient-serving microcomputer 202 services multiple patient operated sensors 204. These sensors 204 are located at a common location, such as a home, and form a basis for monitoring the health status of a group of patients 206 such as family members. The patient operated sensors 204 each serve to take a physiological measurement of a patient 206.

In this embodiment, each of the patient operated sensors 204 has a means for converting the measurement to an indexed record 208. The patient operated sensors 204 and the means for converting the measurement into an indexed record 208 are contained in a sensor housing 209. Each indexed data record includes the type of sensor data recorded. When multiple patients 206 are being monitored, each patient 206 enters a patient identifier code which in turn becomes part of the index of the indexed record.

The indexed data records are stored in a patient site database 210. Patient SPC software 212 is employed to provide instructions for the patient-serving microcomputer 202 to perform a SPC analysis of the indexed data records stored in the patient site database 210, and the means for notifying the patients when Shewhart's rules are met 214 can be internal to the patient-serving microcomputer 202 and provide a response through a peripheral device 216 such as a monitor, printer, etc. Because the indexed data records are encoded with an identification of the type of test and the patient 206, SPC analysis can be performed for the selected set of indexed data records and thus identify for a particular type of test results for a particular patient.

The patient-serving microcomputer 202, the patient site database 210 which may be embodied in software, the patient SPC software 212, and the means for notifying the patient 214 form a patient site 217 with which the means for converting measurements into an indexed data record 208 are interfaced. This can be a direct interface such as a parallel port or a RS-232 port. Alternatively, a data storage unit can be provided in the sensor housing 209 and connected to the patient site database 210 via a patient data modem (not shown) which connects with the patient-serving microcomputer 202.

The patient-HCP interactive health care system 200 also is provided with a modem 218 which communicates between the sensor-serving microcomputer 202 and a health care provider microcomputer 220. The modem 218 preferably allows the patient site microcomputer 202 to transfer the indexed data records from the patient site database 210 to a health care provider site 221 where they are stored in a health care provider database 222, so a health care provider 223 can have continuous access to the data for purposes of analysis with health care provider SPC software 224. The results of this SPC analysis are displayed on an analysis display 225 for review by the health care provider 223.

In the present embodiment, the health care provider 223 has a control program 228, which allows the health care provider 223 to adjust the limits of the patient SPC software 212 through the health care provider microcomputer 220 as the status of each patient 206 changes. The control program 228 also allows the health care provider 223 to adjust the messages which are sent to the peripheral device 216 to fit the needs of a particular patient 206.

It is also preferred that there be a patient note pad 230 provided in the software for both computers, to allow the patients 206 and the health care provider 223 to communicate via their respective computers. It is also possible to establish a bi-directional message center which allows the patient 206 and heath care provider 223 to leave messages.

Figure 4:
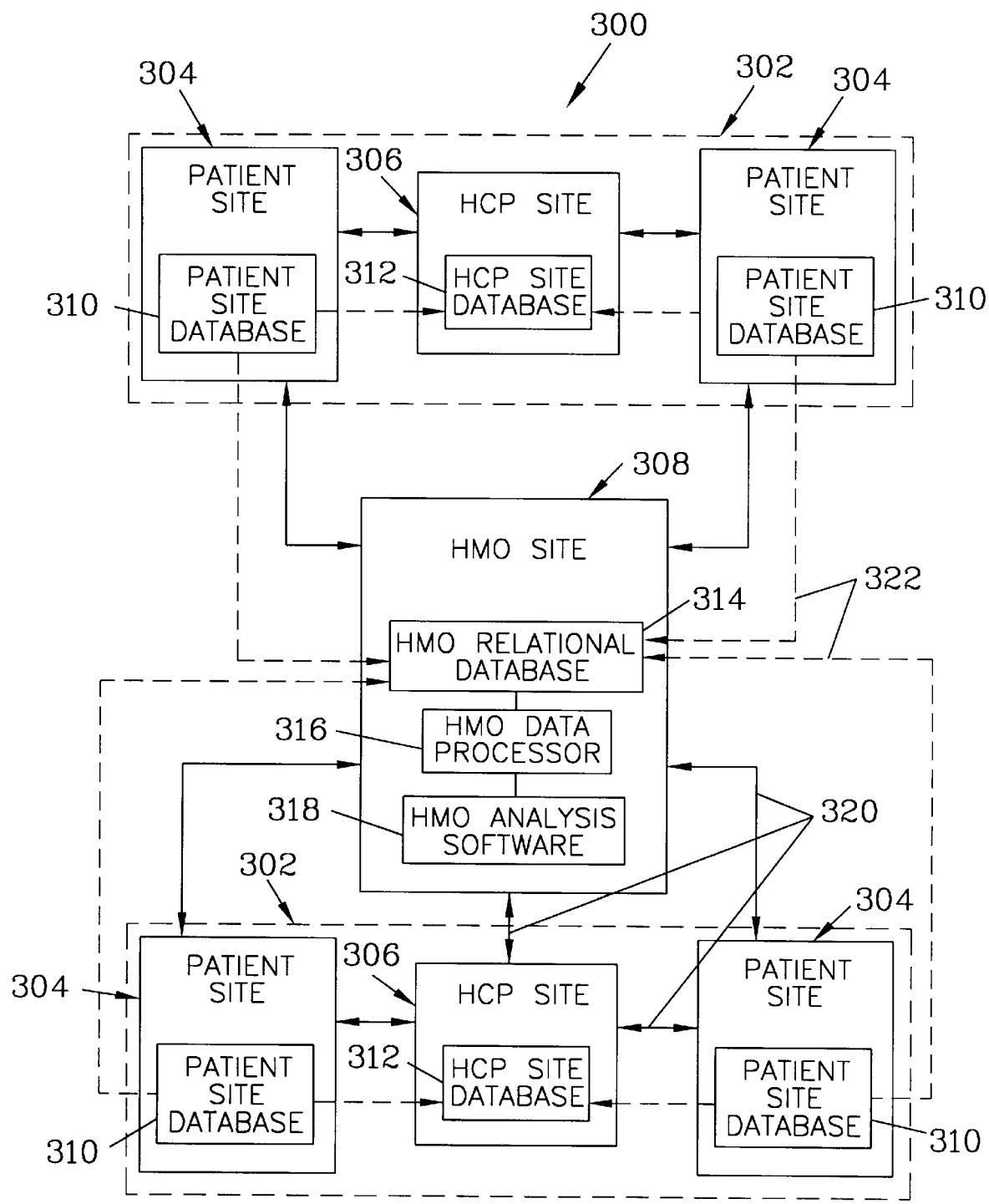
FIG. 4 is another embodiment of the present health care system, which is designed to allow the sharing of data between patients, their health care providers, and a health care organization which oversees the health care for a community of patients.

FIG. 4 is a block diagram which illustrates a community-monitored multi-patient interactive health care system 300. The community-monitored multi-patient interactive health care system 300 differs from the patient-HCP interactive health care system 200 shown in FIG. 3 in that a community of health care providers establish a common depository for patient information, such as an HMO. Such information can be reviewed by the HMO to provide the basis for evaluating the effectiveness of various treatments, comparing the relative effectiveness of the individual health care providers, and/or determining if there are community factors which are affecting the health status of the patients. The HMO can provide non-confidential results of such information to the health care providers and patients for use in developing a more effective treatment program.

In the community-monitored multi-patient interactive health care system 300, there are multiple patient-health care provider interactive systems 302, each of which has a plurality of patient sites 304 and a health care provider site 306, but is otherwise similar to the patient-HCP interactive health care system 200 discussed above. In addition, there is a HMO site 308. The HMO site 308 provides a central location for collection of the data generated at each of the patient sites 304.

Preferably, each of the patient-HCP interactive health care systems 302 is configured as set forth earlier, where data is transferred from patient site databases 310 to a health care provider site database 312. Additionally, it is preferred for the data to also be transferred from the patient site databases 310 directly to a HMO relational database 314. The data from each patient site database 310 is preferably encoded with an additional identifying code to identify the particular health care provider site 306 for the patient(s) at that patient site 304, in addition to the patient identifier and identification of the type of test data. This additional identifying code allows the data to be sorted and processed for each individual health care provider site 306.

The HMO site 308 also has a HMO data processor 316 and associated HMO analysis software 318, which allows for processing community data to permit statistical analysis of the health care data from the individual patient sites 304. Additionally, the HMO data processor 316 and associated HMO analysis software 318 allow independent analysis of the data associated with each of the health care provider sites 306.

It is further preferred that data communicated to the HMO site 308 be provided with additional indices such as location and other environmental influences on the patients. The principals of SPC may also be of benefit to the HMO site 308. In this case, an analysis may be made based on the type of treatment program, seasonal effects, etc. Such analysis can be helpful in statistical studies to determine various factors which affect the health status of patients. Results of such studies can then be communicated from the HMO site 308 to the health care provider sites 306 and the patient sites 304 to assist in improving the effectiveness of the treatment programs for individual patients.

Whether or not such statistical studies are conducted, it is preferred to provide bi-directional communications links 320 between the patient sites 304 and their associated health care provider sites 306, between the patient sites 304 and the HMO site 308, and between each health care provider site 306 and the HMO site 308. The bi-directional communications links 320 allow each party to communicate what it feels is appropriate information to aid in most effectively maintaining the health of the patient. Access must be limited so as not to violate the confidentiality of any of the patients. This is graphically indicated in FIG. 4 by uni-directional data links 322. It should be noted that the bi-directional communications links 320 and the uni-directional data links 322 shown in FIG. 4 are graphical representations, and in reality are typically be combined into single communications channels.

While the embodiment illustrated shows the data being transferred from each patient site 304 directly to the health care provider site database 312 and to the HMO relational database 314, it is possible for the data to be transferred from the patient site database 310 only to the health care provider site database 312, and then from the health care provider site database 312 to the HMO relational database 314. In such cases, the health care provider site 306 includes a means for encoding the indexed data records to identify the particular health care provider site 306. Alternatively, data may be transferred from patient site databases 310 only to the HMO relational database 314. In this case, again, the data from each patient site 304 is encoded with an additional identifying code for the particular health care provider, which allows the data to be downloadable upon request from the HMO relational database 314 to the appropriate health care provider site database 312.

While the above embodiments are for particular systems, it should be appreciated that for any systems having a database of health information on patients representing measurements of a health-related physiological parameter, the use of SPC analysis provides a benefit. In fact, a more generalized method for monitoring the state of health using SPC and control charts is helpful, whether or not it is implemented with a computer, to provide a method for detection of when early intervention is needed to avoid a potential health crisis for a patient.

This method can be initiated by collecting health care data relating to a health condition as the data becomes available and, as the data is collected, calculating control limits for a SPC analysis of the data (as is further described below). Once the limits are established, it is preferred for the data to be charted so as to be readily reviewable by the patient, and more preferably also by the health care provider, so that the data can be visually analyzed.

In practicing the method statistical limits are calculated from the values for the health care test variable in question (X) and from the difference between successive values, the moving range (mR). From these data statistical limits for the data can be calculated. The statistical limits calculated include an average moving range (mRmean), a process center line (Xmean), an upper control limit ($UCL_X$), a lower control limit ($LCL_X$), and an upper limit of the moving range ($UCL_R$). To establish these limits, they are initially calculated according to the following steps after each new test measurement is recorded:

1. The health care test variable values (X) are recorded.

$$X_1, X_2, X_3 \ldots X_n,$$

2. The moving range values (mR) (the difference between successive X values) are calculated according to Equation 1:

$$mR_i = |(X_i - X_{i-1})| \qquad \text{(Equation 1)}$$

and are recorded.

$$mR_2(X_2-X_1) \ldots mR_n(X_n-X_{n-1})$$

3. The process center line (Xmean) (the mean of the data point values) is calculated according to Equation 2:

$$Xmean = \frac{\sum_n X_i}{n} \quad \text{(Equation 2)}$$

and the average moving range (mRmean) (the mean of the moving range values) is calculated according to Equation 3:

$$mRmean = \frac{\sum_{n-1} mR_i}{n-1} \quad \text{(Equation 3)}$$

4. The upper control limit $UCL_X$ for the X values is calculated according to Equation 4:

$$UCL_X = Xmean + (2.66*mRmean) \quad \text{(Equation 4)}$$

and the lower control limit $LCL_X$ for the X values is calculated according to Equation 5:

$$LCL_X = Xmean - (2.66*mRmean) \quad \text{(Equation 5)}$$

5. The upper limit of the moving range $UCL_R$ is calculated according to Equation 6:

$$UCL_R = 3.27*mRmean \quad \text{(Equation 6)}$$

Generally, the control limits are recalculated with each new test measurement throughout the treatment program. However, in some cases, such as where measurements are made very frequently, it may be preferable to establish the control limits based on the calculation for an initial number of data. Classically, SPC analysis has been based on calculating the control limits based on 20 measurements. However, it may be feasible to establish the control limits based on fewer measurement. If the control limits are established, they are maintained at their established values, and thereafter are not recalculated with each new test measurement.

When the statistical limits have been calculated or, if they have been established, as each new test measurement is recorded, the limits are used to apply Shewhart's rules of detection to predict the likelihood of a patient episode where the patient needs immediate care.

Shewhart's rules of detection indicate a special cause variation, which may indicate a potential health crisis, if any of the following conditions are met by the data:

1. One or more variable values are outside the control limits (the data point value is either greater than the $UCL_X$ or less than the $LCL_X$).

2. Eight or more consecutive variable values are on one side of the process center line (data point values are either all greater than or all less than Xmean).

3. Three out of four consecutive variable values are closer to one of the control limits than they are to the process center line.

4. One or more moving range values are above upper limit of moving range (moving range value for data point is greater than $UCL_R$).

If any of these conditions are found in the data, such is considered to indicate a special cause variation. It has been found that a patient should be given immediate attention, since a special cause variation indicates a significant change in the health status of the patient. This change may be an improvement or a deterioration of the health of the patient. In either case, it is likely that the treatment of the patient needs to be adjusted. Particularly, when a deterioration is indicated, a health crisis may occur if no corrective action is taken.

In most cases, the direction of a special cause variation is significant. The direction is determined by the control limit, either the $UCL_X$ or the $LCL_X$, which the data point values appear to be approaching or exceeding. For example, if any data point value were greater than the $UCL_X$, such would constitute a special cause variation in the direction of the upper control limit. Similarly, if eight consecutive data point values were less than Xmean, such would constitute a special cause variation in the direction of the lower control limit.

In many cases, a special cause variation in the direction of one of the limits is desirable, indicating improvement of the patient's health condition, while a special cause variation in the direction of the other control limit is undesirable, indicating deterioration of the patient's health condition. For example, an asthmatic patient's health status would be considered to be improving if his or her values for expiratory flow rate result in a special cause variation in the direction of the upper control limit, indicating increasing flow. Similarly, the patient's health status would be considered to be deteriorating if the values result in a special cause variation in the direction of the lower control limit, indicating decreasing flow rate.

In other cases, a special cause variation in the direction of either limit is undesirable, but the direction is of aid in determining the proper treatment to prevent a health crisis. For example, the health status of an insulin-dependent diabetic patient would be considered to be deteriorating if his or her data point values for blood sugar were to result in a special cause variation in either direction, but the direction would indicate whether the blood sugar were too low, requiring glucose for treatment, or too high, requiring insulin. In all cases where the direction of special cause variations is significant, such direction is preferably noted in the evaluation of the data.

Frequently, a special cause variation, particularly if in the direction indicating improved health, provides indication that a new phase of the treatment program has begun. When a special cause variation occurs, the control limits may need to be reinitialized to reflect the change in the treatment program. Typically, the data preceding those which resulted in the special cause variation is thereafter ignored when calculating the control limits, and the control limits are recalculated as each new measurement is taken. Whether or not a special cause variation indicates a new phase in the treatment program is typically determined by the health care provider.

It is further preferred, for the convenience of the patient and the health care provider, that both the health care test variable in question (X) and the moving range (mR) be plotted on individual axes. Onto this graph are superimposed the average moving range (mRmean), the process center line (Xmean), the upper control limit ($UCL_X$), the lower control limit ($LCL_X$), and the upper limit of the moving range ($UCL_R$). These plots help both the patient and the health care provider better assimilate the data and provide additional appreciation as to the health status of the patient over time.

To assist in visually analyzing for the conditions of Shewhart's rules being met, it is preferred to plot midway lines. The values for the midway lines are calculated as follows:

Upper midway line=$(UCL_X + X\text{mean})/2$

Lower midway line=$(LCL_X + X\text{mean})/2$.

The midway lines are not required for applying Shewhart's rules of detection but, when plotted, assist the care provider and the patient in observing when the third rule of detection indicates a special cause variation, as well as aiding in predicting when such an indication may be imminent.

Additionally, to aid in indicating when one of the rules of detection has been met, it is preferred for the data to be indicated by a line having a particular graphical appearance, such as a certain color or character. If a special cause variation is indicated, the graphical appearance of the line is changed at the data point which caused such. For example, a green colored line might change to red at the point where a special cause variation is indicated. Such change in the graphical appearance of the line is helpful for both patients and care providers in rapidly evaluating the patient's health status.

In cases where the direction of the special cause variation is significant, different graphical appearances, such as two different colors, can be employed to indicate when a special cause variation in the direction of the upper limit is indicated and when a special cause variation in the direction of the lower limit is indicated.

EXAMPLES

To illustrate the suitability of using a method of analysis which employs SPC analysis as part of the method the following examples are provided. The data employed were measured by patients using sensing devices, but were only analyzed retrospectively, and the control limits were calculated based upon all of the data. Since it has been found that the detection of special cause variations with SPC analysis is relatively insensitive to the number of data used to calculate the control limits, similar results would result from analysis performed as the data became available. Thus, had the data been analyzed as it became available, it would have provided its predictive function and given a warning of when the analysis indicated that health status of the patient was approaching a crisis.

FIG. 5 shows an example of an XmR chart 400 displaying peak expiratory flow (PEF) data for a patient with asthma.

The XmR chart 400 is representative of the type of display which could be employed by one of the interactive health care systems discussed above for a patient, and the data was retrospectively analyzed by the method of the present invention.

The data illustrated on the two-part XmR chart 400 are the result of daily tests conducted with a flow meter. The flow meter employed was an AirWatch™ meter produced by ENACT Health Management Systems, and is similar to the flow meter described in the '144 patent. The XmR chart 400 has an upper part 402, where the X values corresponding to the daily PEF measurements are plotted, and a lower part 404, where the moving range differences between successive X values (mR) are plotted.

The upper part 402 displays the observed X values 406, an upper process control limit 408, a process center line 410, a lower process control limit 412, and two midway lines 414. In this example, where PEF is the variable being measured, the upper direction is considered a favorable direction, with increased PEF indicating improvement of the health of the patient, while the lower direction is unfavorable, with decreased PEF indicating deterioration of the health of the patient. The lower part 404 displays the calculated mR values 416, an upper limit of the moving range 418, and an average moving range 420. The control limits (408, 412, and 418) in this example are calculated based on all of the observed data, in the manner discussed in detail above. Thus, in the example shown, the control limits are calculated for n=30.

To generate the XmR chart 400 in the manner discussed earlier, the upper process control limit 408 is determined by calculating the value of Equations 1, 2, and 3 using n=30; the process center line 410 is determined by Equation 1 using n=30; the lower process control limit 412 is determined by calculating the value of Equations 1, 2, and 4 using n=30; the upper limit of the moving range 418 is determined by calculating the value of Equations 2 and 5 using n=30; and the average moving range 420 is determined by Equation 2 using n=30. Once the control limits are plotted, these values and the data can be inspected for instances where Shewhart's rules of detection are met, in which case the health status of the patient is changing significantly and appropriate action should be taken.

If any of the conditions for Shewhart's rules of detection are found in the data, appropriate actions should be taken to either prevent a health crisis or adjust the treatment program accordingly.

It is further preferred, to assist in visually analyzing for the conditions of Shewhart's rules being met, to plot the midway lines 414. The midway lines 414 are not required for applying Shewhart's rules of detection, but assist the health care provider and the patient in observing when the third rule of detection indicates a special cause variation, as well as aiding in predicting when such may be imminent. The midway lines 414 are calculated as follows:

Upper midway line 414a=$(UCL_X + X\text{mean})/2$

Lower midway line 414b=$(LCL_X + X\text{mean})/2$

The XmR chart 400 illustrates where, during the period monitored, Shewhart's rules were met by the data. The group of X values 406' for the dates D15–D18 indicate that the conditions for the third rule are met, since three of four sequential X values 406' are closer to the lower process control limit 412 than to the process center line 410, and thus a notice would be given that preventative action should be taken. As can be seen, the midway lines 414 help in making this situation readily apparent. It should be noted that, even though the next X value 406 shows an apparent correction in the downwards trend, the conditions for the third rule are still met, and the next day the patient required emergency treatment in a hospital. In this particular example, it can be seen that the statistical analysis of the present invention provides a better indication of the state of health of patient than would be possible with the prior art.

Because the data displayed on the XmR chart 400 is for a patient who was not being monitored with the system of the present invention, the patient in this example was not aware of the indication that preventative action should be taken. The next reading, on D19, was higher than the preceding three readings, and was probably interpreted by the patient as a sign of improvement. However, in actuality the health of the patient subsequently deteriorated to a critical health condition, where the patient required emergency room treatment. On the next date for which there was data, D20, the X value 406" dropped below the lower control limit 412 (thus meeting the conditions for the first rule of detection). Had the patient been monitored according to the system of the present invention, the earlier indication of a special cause variation would have provided notice that corrective treatment was necessary, and treatment could have been provided before such a critical condition was reached. This could have provided increased safety to the patient by addressing the problem earlier, and might have avoided the cost and inconvenience of an emergency room visit.

It should be noted that after the patient was treated in the emergency room, a new phase of the treatment program was initiated. The treatment program was altered to include additional medication. This change in treatment resulted in a special cause variation in the positive direction, as shown by the X values 406''', which meet the requirements of the second rule of detection. This special cause variation indicates that the treatment program has entered a new phase, and the control limits (408, 412, and 418) should be reinitialized to reflect that the overall health status of patient has improved. To reinitialize the control limits (408, 412, and 418) the X values 406 preceding the X values 406''' which resulted in the special cause variation (all data prior to D22) are ignored when calculating the control limits. The ability to adjust the control limits (408, 412, and 418) allows the interactive health care system of the present invention to be adapted to best suit the current situation of the patient.

FIG. 6 shows an XmR chart 400' which displays some of the same data as the XmR chart 400, where only the first eighteen X values 406 are plotted to correspond to the results that would be obtained by a patient using the method where the control limits are recalculated after each measurement is taken.

The upper part 402' of the XmR chart 400' displays an instantaneous upper process control limit 408', an instantaneous process center line 410', and an instantaneous lower process control limit 412'. These instantaneous limits (408', 410', and 412') are calculated based upon the first eighteen X values 406, in order to correspond to the limits that would be calculated after the eighteenth measurement was taken. Similarly, the lower part 404' of the XmR chart 400' displays an instantaneous upper limit of the moving range 418', and an instantaneous average moving range 420', which are calculated based upon the first seventeen mR values 416.

It can be seen that the group of X values 406' indicates a special cause variation in the direction of a deterioration in health status, since three out of four consecutive X values 406' are closer to the instantaneous lower process control limit 412' than to the instantaneous process center line 410'. Thus, had the patient been using the method where the limits are recalculated after each measurement is taken, and the data analyzed to determine whether the conditions of Shewhart's rules are met, this special cause variation would have provided notice to the patient to take action to avoid the potential health crisis which resulted in a hospital visit.

FIG. 7 shows another example, an XmR chart 500 displaying blood glucose level data for a patient with diabetes. Again, the actual data displayed on the XmR chart 500 illustrated were retrospectively analyzed using SPC techniques.

The data illustrated on the two-part XmR chart 500 are the result of daily tests conducted with a device for measuring blood glucose level. Again, the XmR chart 500 has an upper part 502, where the X values corresponding to the daily blood glucose measurements are plotted, and a lower part 504, where the moving range differences between successive X values (mR) are plotted.

The upper part 502 displays the observed X values 506, an upper process control limit 508, a process center line 510, a lower process control limit 512, and two midway lines 514. In this example, the lower direction is considered a favorable direction, with decreased blood glucose indicating improvement of the health of the patient, while the upper direction is unfavorable, with increased blood glucose indicating deterioration of the health of the patient. The lower part 504 displays calculated mR values 516, an upper limit of the moving range 518, and an average moving range 520. Again, the control limits (508, 512, and 518) in this example are calculated based on all of the observed data, in the manner discussed in detail above. Thus, in the example shown, the control limits are again calculated for n=30.

The data plotted on the XmR chart 500 are for a non-insulin-dependent patient who began a new treatment using an oral hypoglycemic medication. The XmR chart 500 helps to evaluate the effectiveness of such treatment, by illustrating where Shewhart's rules are met by the measurement data. The group of X values 506' for the dates D23–D30 indicate that the conditions for the second rule are met, since eight sequential X values 506' are on one side of the process center line 510. In this case, since the X values 506' are all lower than the process center line 510, which is the favorable direction, a notice would be given that a positive special cause variation occurred, indicating a significant improvement in the health status of the patient in response to the treatment.

It should be noted that during the period monitored, there are two X values 506" which are relatively high compared to the initial values, while the X values 506' which resulted in a special cause variation are relatively close to the initial values. Had these data been analyzed by a simple comparison to an initial value, such as is taught in the '144 patent, it is likely that the X values 506" would have resulted in a false alarm to the patient, while the significance of the X values 506' might have been missed. Again, the statistical analysis of the present invention provides a better indication of the state of health of patient than would be possible with the prior art.

While the novel features of the present invention have been described in terms of particular embodiments and preferred applications, it should be appreciated by one skilled in the art that substitution of materials and modification of details obviously can be made without departing from the spirit of the invention.

What I claim is:

1. An interactive health care system for a patient located at a patient site and under the care of a health care provider located at a health care provider site physically separated from the patient site, the interactive health care system providing for patient participation in the patient's health care, the system comprising:

at least one patient operated sensor for obtaining measurement of a patient's physiological parameters;

means for converting each measurement into an indexed data record;

a patient site data processing unit for sorting and processing said indexed data records;

an associated patient site database which stores said indexed data records;

an instruction set for said patient site data processing unit for enabling said patient site data processing unit to selectively perform a SPC analysis on said indexed data records, said SPC analysis including the establishment of an XmR control chart having calculated process control limits, a calculated process center line, and a calculated upper limit of the moving range, and to test whether the conditions of one or more of the following rules are met,
1. one or more variable values corresponding to said measurements are outside said process control limits,
2. eight or more consecutive variable values are on one side of said process center line,
3. three out of four consecutive variable values are closer to one of said control limits than they are to said process center line, or
4. one or more moving range values defined as the difference between subsequent variable values are above said upper limit of the moving range; and means for notifying the patient when one or more of the above four rules of detection are met.

2. The interactive health care system of claim 1 wherein said patient site data processing unit is a patient operated microcomputer and said instructional set for selectively performing SPC analysis is software compatible with said patient operated microcomputer, and further wherein the interactive health care system further comprises:

a health care provider microcomputer;

means for providing a communication link between said health care provider microcomputer and said patient operated microcomputer.

3. The interactive health care system of claim 2 wherein the interactive health care system further comprises:

a health care provider database for storing said indexed data record;

means for transmitting said indexed data record to said health care provider data base and indexing with respect to source;

health care provider SPC software for said health care provider microcomputer for analyzing and testing said indexed data records contained in said health care provider data base to determine if any of the four rules of detection are met; and means for notifying the health care provider as to when said data meet one or more of the four rules.

4. The interactive health care system of claim 3 wherein the interactive health care system handles multiple patients and each of said indexed data records is further indexed with regard to patient identity, and said health care provider SPC software analyzes said indexed data records in said health care provider database on an individual patient basis.

5. The interactive health care system of claim 4 wherein said means for notifying the patient when one or more of the four rules of detection are met provides a message on said patient operated microcomputer of each of the patients for whom the four rules of detection are met, said message advising the patient to notify his/her health care provider.

6. The interactive health care system of claim 4 wherein said means for notifying the patient when one or more of the four rules of detection are met is a patient look-up table, said patient look-up table providing a message specified by the health care provider based on the historical data of the patient.

7. A method for evaluation of the status of health of a patient under the indirect supervision of a health car provider, the patient measuring a physiological parameter which is indicative of the patient's state of health, the method comprising the steps of:

collecting health care data values related the patient;

recording said data values;

calculating SPC control limits ($UCL_X$, $LCL_X$, Xmean, and $UCL_R$);

testing for one or more of the following four rules of detection being met by said data values and said SPC control limits:
one or more data values being either greater than the $UCL_X$ or less than the $LCL_X$,
eight or more consecutive data values being either all greater than or all less than Xmean,
three out of four consecutive data values being closer to either the $UCL_X$ or the $LCL_X$ than to Xmean,
one or more moving range values, defined as the difference between subsequent data values, being greater than $UCL_R$; and if the conditions for one or more of the above four rules of detection are met, providing notice to the patient to take corrective action.

8. The method of claim 7 wherein said corrective action is for the patient to contact the health care provider and supply the data to the health care provider.

9. The method of claim 7 wherein said step of testing for one or more of the four rules of detection being met further comprises the steps of:

plotting said data values as a function over time on a first set of axes after they are recorded;

plotting said $UCL_X$, said $LCL_X$, and said Xmean on said first set of axes;

plotting said moving range values calculated for said data values, said moving range values being plotted as a function over time on a second set of axes;

plotting said $UCL_R$ on said second set of axes,
said first set of axes, said second set of axes, and said plotted values in combination forming an XmR chart; and visually inspecting to see if conditions for one or more of the four rules of detection are met.

10. The method of claim 9 wherein if one of the conditions for the four rules of detection is met, the character of the line connecting the point is changed.

* * * * *